(12) United States Patent
Rephaeli et al.

(10) Patent No.: US 10,375,330 B2
(45) Date of Patent: Aug. 6, 2019

(54) SYSTEMS AND METHODS FOR SURFACE TOPOGRAPHY ACQUISITION USING LASER SPECKLE

(71) Applicant: VERILY LIFE SCIENCES LLC, Mountain View, CA (US)

(72) Inventors: Eden Rephaeli, Mountain View, CA (US); Daniele Paolo Piponi, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 257 days.

(21) Appl. No.: 15/592,622

(22) Filed: May 11, 2017

(65) Prior Publication Data

US 2017/0347043 A1 Nov. 30, 2017

Related U.S. Application Data

(60) Provisional application No. 62/342,758, filed on May 27, 2016.

(51) Int. Cl.
*H04N 5/357* (2011.01)
*A61B 1/05* (2006.01)
(Continued)

(52) U.S. Cl.
CPC .............. *H04N 5/357* (2013.01); *A61B 1/05* (2013.01); *A61B 1/0661* (2013.01);
(Continued)

(58) Field of Classification Search
CPC combination set(s) only.
See application file for complete search history.

(56) References Cited

U.S. PATENT DOCUMENTS

2005/0231465 A1 10/2005 DePue
2013/0202196 A1* 8/2013 Shirley .............. G01B 9/02004
382/154
(Continued)

FOREIGN PATENT DOCUMENTS

WO 2007/149602 12/2007

OTHER PUBLICATIONS

Jakobsen, M.L., et al., "Distance Measurements by speckle correlation of objective speckle patterns, structured by the illumination," Applied Optics, p. 4316-6600 (2012).
(Continued)

*Primary Examiner* — Behrooz M Senfi
(74) *Attorney, Agent, or Firm* — McDonnell Boehnen Hulbert & Berghoff LLP

(57) ABSTRACT

The present disclosure relates to systems and devices configured to determine the distance to objects within a field of view. Namely, at least a portion of the field of view may be illuminated with a coherent light source. Due to interactions between the laser light, the transmission medium, and the object, characteristic laser speckle patterns may be formed. These characteristic laser speckle patterns may be imaged with a camera. Using statistical image analysis, an estimated distance to the objects within the field of view may be obtained. For example, the image frame may be partitioned into a plurality of image segments. An autocorrelation for each image segment of the plurality of image segments may be obtained. A depth map may be obtained based on the autocorrelations.

20 Claims, 11 Drawing Sheets

(51) Int. Cl.
*A61B 5/00* (2006.01)
*G01B 9/02* (2006.01)
*A61B 1/06* (2006.01)
*H04N 5/225* (2006.01)
*G01B 11/24* (2006.01)
*G06T 7/521* (2017.01)
*G06T 7/529* (2017.01)
*A61B 5/107* (2006.01)

(52) U.S. Cl.
CPC ........ *A61B 5/0066* (2013.01); *G01B 9/02094* (2013.01); *G01B 11/24* (2013.01); *G06T 7/521* (2017.01); *G06T 7/529* (2017.01); *H04N 5/2256* (2013.01); *A61B 5/0084* (2013.01); *A61B 5/1072* (2013.01); *A61B 5/1076* (2013.01); *A61B 5/7246* (2013.01); *G06T 2207/20021* (2013.01); *G06T 2207/20056* (2013.01); *H04N 2005/2255* (2013.01)

(56) References Cited

U.S. PATENT DOCUMENTS

2017/0180708 A1* 6/2017 Hazeghi ............... H01S 5/0654
2019/0068951 A1* 2/2019 Mor .................. G02B 27/0983

OTHER PUBLICATIONS

Patzelt, Stefan, et al. "Parametric optical surface roughness measurement by means of polychromatic speckle autocorrelation." Proc. SPIE. vol. 3426. 1998.
International Search Report, International Application No. PCT/US2017/032127, dated Sep. 6, 2017.

\* cited by examiner

Cross-Section view

Cross-Section view

SYSTEMS AND METHODS FOR SURFACE TOPOGRAPHY ACQUISITION USING LASER SPECKLE

CROSS-REFERENCE TO RELATED APPLICATIONS

The present application is a non-provisional patent application claiming priority to Provisional Patent Application No. 62/342,758, filed May 27, 2016, the contents of which are hereby incorporated by reference.

BACKGROUND

Unless otherwise indicated herein, the materials described in this section are not prior art to the claims in this application and are not admitted to be prior art by inclusion in this section.

Laser light speckle is a pattern that is observable when a coherent light source interacts with a surface and/or a scattering transmission medium, such as air or an optical fiber. For example, the effect can be observed when a visible laser pointer interacts with a projector screen. Speckle occurs due to optical interference between relative optical phases arriving at a detector by traveling over a distribution of distances. As such, interactions between a laser beam and a diffusive surface (e.g., paper or white paint) may result in observable speckle patterns.

SUMMARY

In a first aspect, a system is provided. The system includes at least one laser light source, an image sensor, and a controller. The controller includes a memory and at least one processor. The at least one processor executes instructions stored in the memory to carry out operations. The operations include causing the at least one laser light source to illuminate a field of view with coherent laser light so as to form a characteristic laser speckle pattern. The operations also include causing the image sensor to capture an image frame. The image frame includes information indicative of the characteristic laser speckle pattern. The operations additionally include partitioning the image frame into a plurality of image segments and determining an autocorrelation for each image segment of the plurality of image segments. The operations also include, based on the autocorrelations, determining a depth map of the field of view.

In a second aspect, a method is provided. The method includes illuminating a field of view with a characteristic laser speckle pattern of at least one laser light source. The method also includes capturing, with an image sensor, an image frame. The image frame includes information indicative of the characteristic laser speckle pattern. The method additionally includes partitioning the image frame into a plurality of image segments. The method yet further includes determining an autocorrelation for each image segment of the plurality of image segments. The method includes, based on the autocorrelations, determining a depth map of the field of view.

Other aspects, embodiments, and implementations will become apparent to those of ordinary skill in the art by reading the following detailed description, with reference where appropriate to the accompanying drawings.

DETAILED DESCRIPTION

Figure 1A:
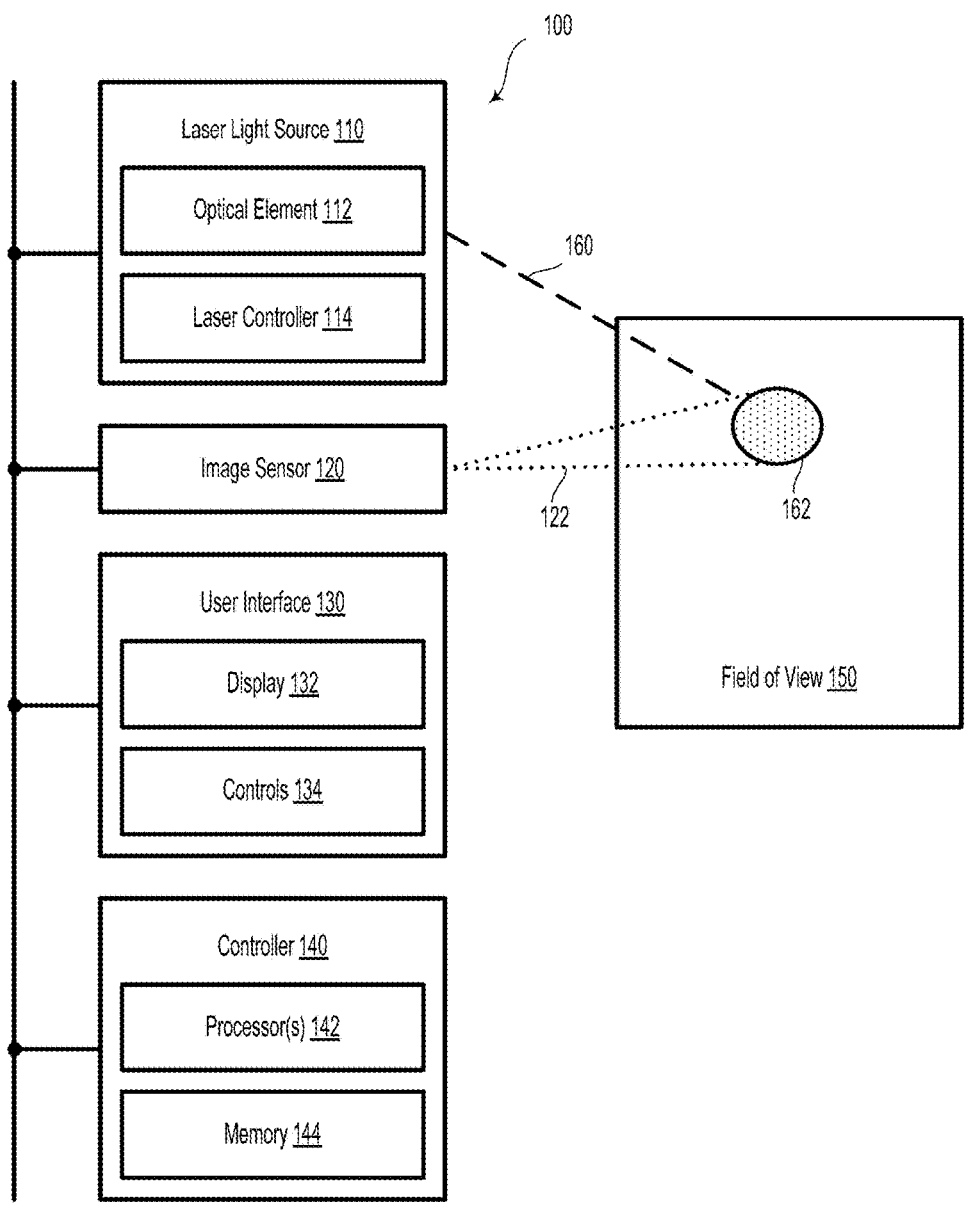
FIG. 1A is a block diagram of a system according to an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

While the present disclosure describes embodiments for use in vivo, one of skill in the art will also recognize that in vitro and ex vivo applications are possible as well. Further, while embodiments disclosed herein make reference to use on or in conjunction with a living human body, it is contemplated that the disclosed methods, systems and devices may be used in any environment where measuring and/or estimating a distance to an object or surface may be desirable. For example, one of skill in the art will recognize that the embodiments disclosed herein may be used to map the depth of objects in a field of view.

Overview

Systems, devices, and methods described herein may relate to determining a distance to one or more targets. As such, the techniques disclosed herein may be applied to provide non-contact, optical depth-mapping of a scene. Specifically, the systems and methods herein relate to determining distance to targets based on statistical image processing of a characteristic laser speckle pattern.

Depth-sensing applications can make use of devices capable of obtaining a full field-of-view depth map in compact form-factors. In the field of surgical robotics, where endoscopes are often used, there exists a great challenge in obtaining rapid, robust and accurate depth maps due to the extremely compact form-factor inherent in endoscopes. The distance and angle between the light source and the camera used in triangulation-based depth sensing or structured illumination schemes is small, and therefore acts to limit the precision and accuracy of such depth readings.

Methods using structured light projection and/or laser beam scanning may slow down the speed of depth map acquisition. This may be problematic when the object(s) in the field-of-view is/are moving. Specifically, motion blur may lead to uncertainty in topography calculation. For example, depth mapping using point-by-point triangulation may be difficult or impossible using such methods because the depth map will represent the topography of different points in the scene at different times. Furthermore, depth mapping using structured light illumination schemes may fail completely.

The methods and systems described herein use a coherent light source to create an observable speckle pattern within a field of view. Furthermore, the speckle pattern may be segmented using a segmentation algorithm. The segmentation algorithm may be used to parse the field-of-view into iso-height or quasi iso-height surfaces. The speckle intensity distribution is captured by a camera and the autocorrelation of the speckle pattern is calculated, using a sequence of coarse to fine windows (i.e. sub-areas or regions of interest (ROIs) of the field-of-view). By refining the area windows, one can determine the boundaries between different height surfaces. By beginning the image analysis by starting with coarse windows and then refining the window size, one may robustly determine the smallest window to use for a given region of the field of view. It is within this smallest window in which the autocorrelation function of the speckle image may be calculated. A result of the autocorrelation function may include a central peak. The shape of such a central peak (e.g., a full-width half-maximum) is directly proportional to $\lambda \times (z/d)$, where $\lambda$ is the wavelength of light, z is the distance to surface, and d is the aperture of light beam.

Methods and systems described herein contemplate a variety of ways to provide wavelength diversity in the laser speckle so as to provide statistically independent speckle images. Using statistically independent speckle images may improve the reliability of depth maps. As an example, more than one laser may be used. The multiple lasers may be configured to emit the same wavelength or different wavelengths with respect to one another. In an alternative embodiment, the laser beam(s) may be passed through a moving diffuser and/or may be passed through a variable beam aperture using optics or irises. Alternatively or additionally, the optical focal length may be adjusted with a moving diffuser or a fluttering aperture.

By creating wavelength diversity and/or statistical diversity, multiple statistically-independent speckle patterns may be obtained within a brief amount of time (e.g., to minimize the effect of object and/or camera motion). Such techniques directly increase the probability that the depth at each point in the field of view may be calculated with a high degree of confidence.

System Examples

The present disclosure relates to systems and devices configured to determine the distance to objects within a field of view. Namely, at least a portion of the field of view may be illuminated with a coherent light source. Due to interactions between the laser light, the transmission medium, and the object, characteristic laser speckle patterns may be formed. These characteristic laser speckle patterns may be imaged with a camera. Using statistical image analysis, an estimated distance to the objects within the field of view may be obtained.

FIG. 1A is a block diagram of a system 100 according to an example embodiment. System 100 includes a laser light source 110, an image sensor 120, a user interface 130, and a controller 140.

Laser light source 110 may be configured to illuminate a field of view 150 with a laser beam 160, which may form a characteristic speckle pattern 162. Laser light source 110 is a coherent light source that may exhibit high temporal coherence (e.g., narrow wavelength emission) and/or high spatial coherence (e.g., highly collimated or focused beam). Additionally or alternatively, laser light source 110 may be configured to defocus a laser beam to illuminate at least a portion of a field of view 150.

Laser light source 110 may be a continuous laser source or a pulsed laser source. Furthermore, laser light source 110 may be configured to emit one or more wavelengths of light. For example, laser light source 110 may emit laser light having a wavelength of 635 nm. Additionally or alternatively, laser light source 110 may emit laser light at a wavelength of 445 nm. Other emission wavelengths, both inside and outside the visible light spectrum, are contemplated. In an example embodiment, the laser light source 110 may emit a plurality of laser wavelengths. In such a scenario, the characteristic laser speckle pattern 162 may include at least two laser wavelengths from the plurality of laser wavelengths.

Laser light source 110 may include a variety of different types of light sources that emit coherent light. For example, laser light source 110 may be a gas laser (e.g., HeNe), which may include an excimer laser. Alternatively, laser light source 110 may include a solid-state laser, a dye laser, a fiber laser, or a semiconductor laser. In some embodiments, laser light source 110 may include multiple laser sources. For example, laser light source 110 may include an excimer cutting laser (e.g., for tissue ablation) and a HeNe illumination laser for depth-mapping purposes as described herein.

Additionally or alternatively, the cutting laser and the illumination laser may be combined into a single light source. In such a scenario, laser light source 110 and laser beam 160 may provide the characteristic speckle pattern 162. Laser light source 110 may also be configured to provide a surgical laser beam, which may be suitable for cutting tissue and/or other materials. That is, laser light source 110 may be configured to operate according to different operational modes, such as a low power (imaging/depth-mapping) mode, and a high power ablation/material removal mode. Other ways to operate laser light source 110 are possible and contemplated herein.

Laser light source 110 may include an optical element 112 and a laser controller 114. Optical element 112 may include a beam expander, a focusing lens, an aperture, an optical fiber, or another type of optical element configured to focus, defocus, modify, or steer the laser beam 160, which may change the characteristic speckle pattern 162. In an example embodiment, the optical element 112 may be controlled by the laser controller 114 or controller 140. Optical element 112 may be configured to steer the laser beam 160 so as to illuminate various portions of the field of view 150 with coherent laser light to form the characteristic speckle pattern 162.

Laser controller 114 may be configured to control certain aspects of operation of laser light source 110. For example, laser controller 114 may be configured to trigger the emission of laser light from laser light source 110. Additionally or alternatively, laser controller 114 may be configured to adjust a laser power, an emission wavelength, or other aspects of laser light emission from laser light source 110. Laser controller 114 may be additionally or alternatively configured to adjust optical element 112. For example, laser controller 114 may continually or intermittently wobble, or otherwise adjust, a position of an optical lens so as to change various aspects of characteristic speckle pattern 162.

The characteristic speckle pattern 162 is a random intensity pattern formed by interference between wavefronts that make up the laser beam 160. The characteristic speckle pattern 162 may change based on, for example, the surface from which it is reflected as well as the distance to that surface (with respect to laser light source 110), changes in the transmission medium, or adjustments with the optical path of laser beam 160. Some characteristic speckle patterns may appear as a plurality of points or dots with a finite radius. Additionally or alternatively, speckle patterns may appear to "boil" or otherwise dynamically change shape.

Various techniques described herein may relate to a statistical analysis of images of characteristic speckle pattern 162. In some embodiments, a depth map of field of view 150 may be obtained by analysis of one or more autocorrelations of such images.

Image sensor 120 may include an array of discrete photodetectors, or image pixels. For example, image sensor 120 may include a focal plane array (FPA) that includes a plurality of charge-coupled devices (CCDs) or complementary metal-oxide semiconductor (CMOS) devices. Image sensor 120 may be configured to provide image information, in the form of still images or video images, to user interface 130 and/or controller 140.

In an example embodiment, the image sensor 120 may be configured to capture images of the field of view 150 using exposure conditions similar to conventional digital image capture. However, exposure times faster than ⅟₆₀s may provide less object and/or camera motion blur, and lead to more reliable distance estimates.

In some embodiments, image sensor 120 may be configured to capture images of an entire field of view 150. Additionally or alternatively, image sensor 120 may be configured to capture images of a portion of the field of view 150. For example, image sensor 120 may be optically coupled to one or more of a lens, a movable/deformable mirror, or another type of controllable optical element. In such a scenario, a viewable angle 122 of image sensor 120 may be adjustable. Furthermore, image sensor 120 may be configured to move with respect to the field of view so as to capture image information from different portions of the field of view 150.

In some embodiments, image sensor 120 may be activated or initiated by a signal (e.g., a trigger signal or a clock signal) from laser controller 114 or controller 140. That is, image capture via image sensor 120 may be synchronized to coincide with light emission from laser light source 110 or a given beam position of laser beam 160.

Image sensor 120 may be configured to sense light at one or more wavelengths. As an example, image sensor 120 may include a Bayer filter or another type of color filter such that some image pixels may receive a desired wavelength or range of wavelengths. Such a filter may enable image sensor 120 to provide multi-color imaging.

User interface 130 may include a display 132 and controls 134. In an example embodiment, the user interface 130 may provide a way for a user to interact with the system 100. Display 132 may include an LED display configured to provide information indicative of distances to certain objects within the field of view. For example, the display 132 may provide a live view representation of the field of view of the image sensor 120. Furthermore, a depth map may be overlaid on the live view representation or displayed in a side-by-side view. The depth map may include one or more of: numerals or text indicating absolute distance units (e.g. "2.53 mm"), a color-mapped representation of the distance to various regions or objects within the field of view (e.g., a "heat" or rainbow-color map), or a topographical-style line map indicating iso-distance or pseudo-iso-distance features. Other ways to provide distance information via display 132 are contemplated. Alternatively or additionally, display 132 may be operable to provide notifications, information, and/or options to a user of system 100.

Controls 134 may include a touch screen, touch pad, and/or one or more buttons. Additionally or alternatively, controls 134 may include a voice recognition system, a gesture recognition system, or a foot pedal. In an example embodiment, controls 134 may provide a way for a user to adjust settings, provide feedback, or otherwise control system 100. Other ways of controlling system 100 via user interface 130 are contemplated.

The communication interface 118 may include hardware and/or software configured to enable wireless communication between system 100 and other devices. For example, the communication interface may enable messaging and/or data transfers between the system 100 and a cloud-computing server.

While FIG. 1 illustrates system 100 as having a single laser light source 110 and a single image sensor 120, it is understood that any number of laser sources and image sensors may be included as elements within system 100.

The controller 140 of system 100 may include a processor 142 and a memory 144. Processor 142 may execute instructions stored in memory 144. As such, controller 140 may be operable to perform operations, some of which may involve other elements of system 100. For example, controller 140 may be operable to cause laser light source 110 to illuminate a field of view 150 with coherent laser light so as to form a characteristic laser speckle pattern 162. That is, controller 140 may provide a trigger or enable signal to the laser light source 110 so as to cause it to illuminate the field of view 150. Additionally or alternatively, controller 140 may control optical element 112 and/or laser controller 114 so as to indirectly steer or enable laser light to be emitted from the laser light source 110 and to impinge upon the field of view 150 so as to cause the characteristic speckle pattern 162.

Controller 140 may also be operable to cause the image sensor 120 to capture an image frame. For example, the image frame may include information indicative of the characteristic laser speckle pattern. The image frame may include digital information (e.g., a digital photograph) about the scene. The digital information in the image frame may be formatted according to a variety of different digital image formats. For example, the image frame may be formatted according to Joint Photographic Experts Group compression method (JPG), tagged image file format (TIFF), Portable Network Graphics (PNG), Graphics Interchange Format (GIF), WebP, RAW camera format, or another type of image format.

In an example embodiment, the image frame may include information about an intensity of light impinging on a given pixel of the image sensor 120. In some examples, the image frame may include multi-color information. In other examples, the image frame may be monochromatic, such as a grayscale image.

Controller 140 may be operable to partition the image frame into a plurality of image segments. That is, controller 140 may partition the image frame into several image portions. In an example embodiment, the as-captured image frame could have pixel dimensions of 4096×2160 pixels. In such a scenario, the controller 140 may partition the as-captured image frame into tiled image segments each having 128×72 pixels. That is, the as-captured frame may be broken up into 32×30 image segments.

Controller 140 may determine an autocorrelation result for each image segment of the plurality of image segments. The autocorrelation result may be determined by the autocorrelation function (ACF), which is given by the expression:

$$R(x,y)=f(x,y)\times f(x,y)=\int_{-\infty}^{+\infty}\int_{-\infty}^{+\infty} f(x',y') \cdot f(x+x',y+y') \, dx'dy'$$

where f(x,y) is the two-dimensional brightness function that defines the image, and x' and y' are dummy variables of integration.

The ACF provides a two-dimensional function that describes how well an image correlates with itself when the image is displaced with respect to itself in all possible directions in the x,y plane.

In an example embodiment, a Fourier transform, such as a fast Fourier transform (FFT) may be used to calculate the ACF. For example, determining the autocorrelation for each image segment may include determining a power spectrum of the respective image segment. In such a scenario, the power spectrum of the respective image segment may include a square of a Fourier transform of an image intensity of the respective image segment.

By calculating the ACF for each image segment, information about the local region of the field of view may be determined. In an example embodiment, each autocorrelation result may be proportional to an approximate distance to an object or objects within that image segment.

The ACF will exhibit a central peak, the "cross-sectional" shape (as plotted along the x or y axis) of which depends upon the feature shape and/or grain size of the image.

Based on the autocorrelations, controller 140 may be configured to determine a distance to each image segment. The respective distances may be used to form a depth map of distance information within the field of view. That is, the shape of a central peak of R(x,y) is directly proportional to $\lambda.33$ (z/d), where $\lambda$ is the wavelength of laser light, z is the distance to the surface, and d is the aperture of the laser beam. As such, perhaps with the additional aid of an initial calibration, the distance z may be determined because the laser wavelength and beam diameter are known a priori.

In an example embodiment, the image frame may include one image frame from a plurality of image frames of the field of view captured successively, or at least at different points in time. In such a scenario, the depth map of the field of view may include averaging the respective autocorrelation information from corresponding image segments of the plurality of image frames.

The controller 140 and/or the laser controller 114 may be configured to adjust a variety of different elements of the system 100, particularly to change the statistical autocorrelation analysis in determining a depth map. As such, the controller 140 and/or the laser controller 114 may be configured to: cause the laser light source to move, interpose a moving diffuser between the at least one laser light source and the field of view, adjust an optical path of light emitted by the at least one light source to illuminate the field of view, or adjust an operating condition of the at least one laser light source.

Optionally, system 100 may include a battery or another type of power supply (not illustrated). The battery may include a primary (non-rechargeable) or a secondary (rechargeable) battery. In an example embodiment, the battery may include a thin film cell battery. Furthermore, in an example embodiment, battery may include an alkaline battery, a nickel-metal-hydride battery or a lithium-ion battery. Other types of batteries or power supplies are possible.

Additionally or alternatively, system 100 may include a communication interface (not illustrated). The communication interface may be operable to establish a communication link between various elements of system 100 and/or external systems via one or more communication protocols. For example, the communication interface may be configured to provide a communication link between controller 140, laser light source 110, image sensor 120, and user interface 130 via a BLUETOOTH LOW-ENERGY (BLE), ZIGBEE, and/or Wi-Fi communication protocol. Additionally or alternatively, the communication interface may be established via near-field communication (NFC) and/or radio-frequency identification (RFID). Other types of communication protocols are possible and contemplated herein.

Figure 1B:
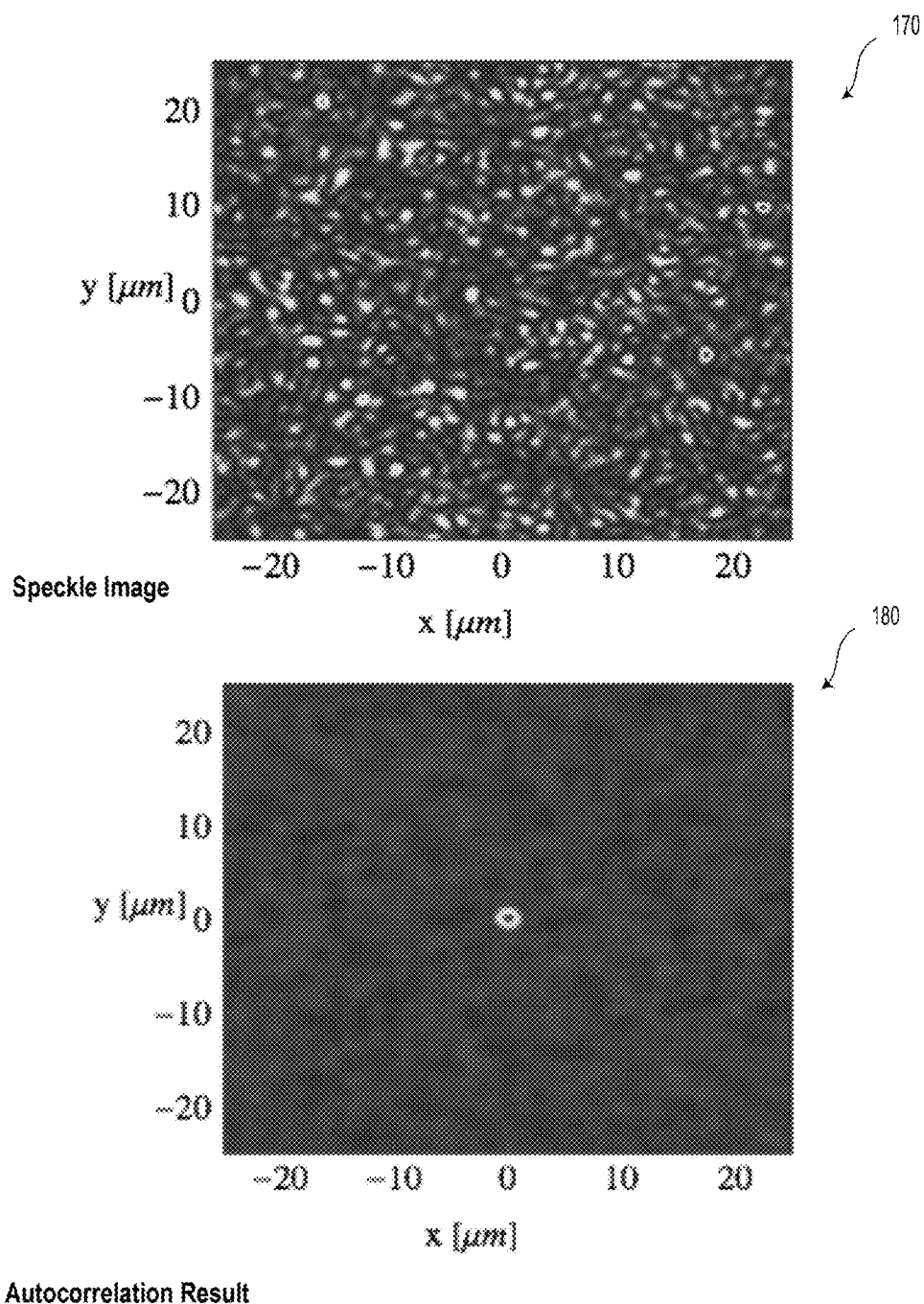
FIG. 1B illustrates a speckle image and autocorrelation result according to an example embodiment.

FIG. 1B illustrates a speckle image 170 and autocorrelation result 180 according to an example embodiment. Speckle image 170 may be similar or identical to the image frame described with regard to FIG. 1A. Namely, speckle image 170 may include a two-dimensional representation of an intensity of at least a portion of the characteristic speckle pattern 162. As illustrated, speckle image 170 may include "grains," "dots," or "blobs" having a unique arrangement and size. In some embodiments, the speckle image 170 may include a distance scale along the x and/or y directions.

Autocorrelation result 180 may be a two-dimensional representation of the ACF as described with regard to FIG. 1A. The autocorrelation result 180 may include a distance scale similar to that of the speckle image 170. Additionally, the autocorrelation result 180 may include a central peak. The shape of the central peak may depend upon the size and shape of the features within the speckle image 170 as well as upon the distance between the laser light source 110 and the surface on which the speckle image 170 is observed.

Figure 1C:
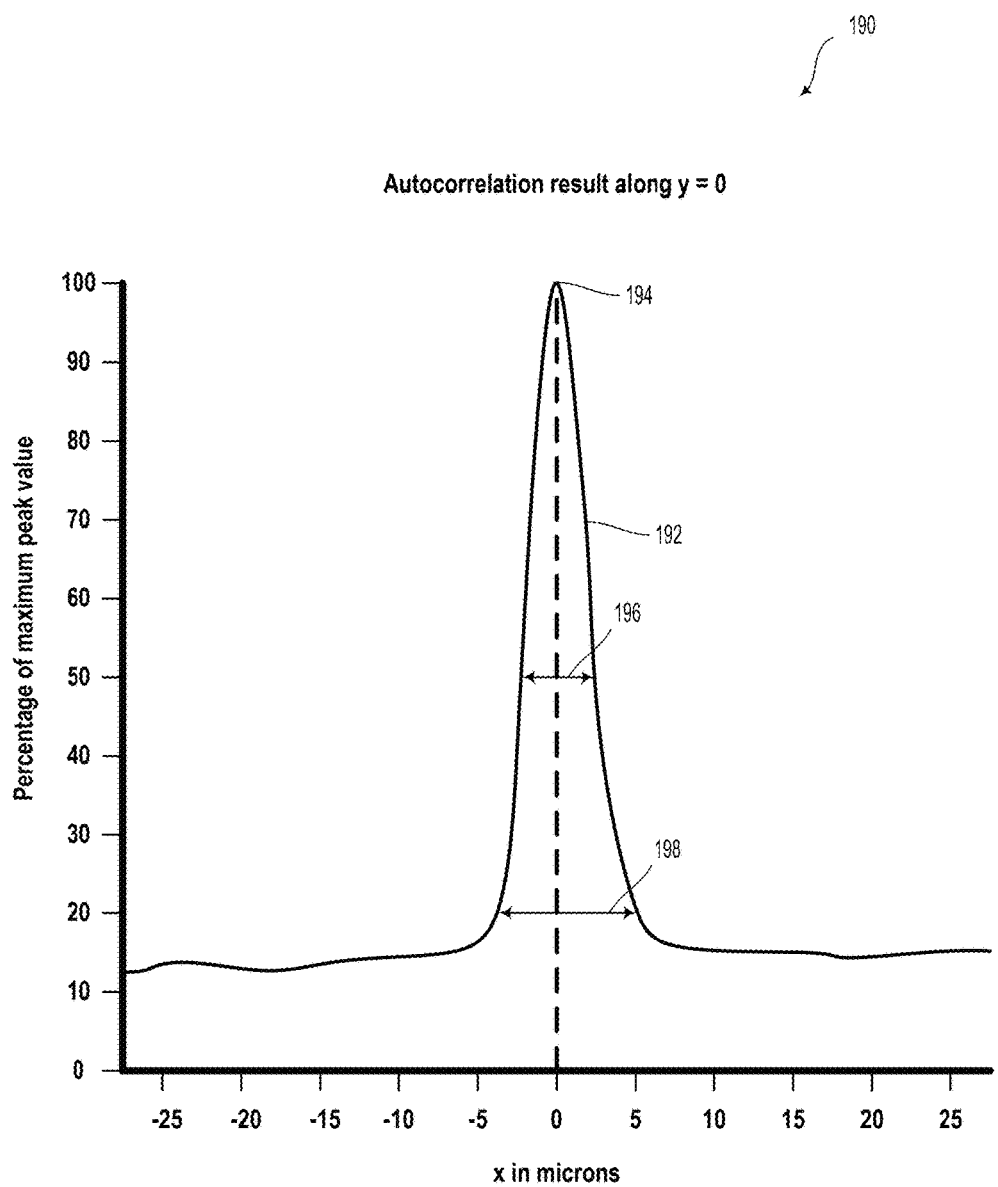
FIG. 1C illustrates an autocorrelation result according to an example embodiment.

FIG. 1C illustrates an autocorrelation result 190 according to an example embodiment. Autocorrelation result 190 may be a representation of autocorrelation data 192 along a line where y=0. Autocorrelation data 192 includes a central peak 194 and a full width half maximum (FWHM) 196. The FWHM 196 is approximately 5 microns in this case, but other values are possible.

For a given operating condition, (e.g., laser power, surface type, optical path) the FWHM 196 or another measure (e.g., full width, 20% max 198) of the autocorrelation data 192 may correspond to an estimated distance to the object or objects in the given field of view (or portion thereof). In this case, for example, a FWHM of 5 microns may relate to a distance-to-object of 2.5 cm. Other FWHM/distance relationships are possible.

Furthermore, although FWHM 196 includes a value for y=0, average FWHM (e.g., in all directions moving away from the origin) is also possible.

Figure 2A:
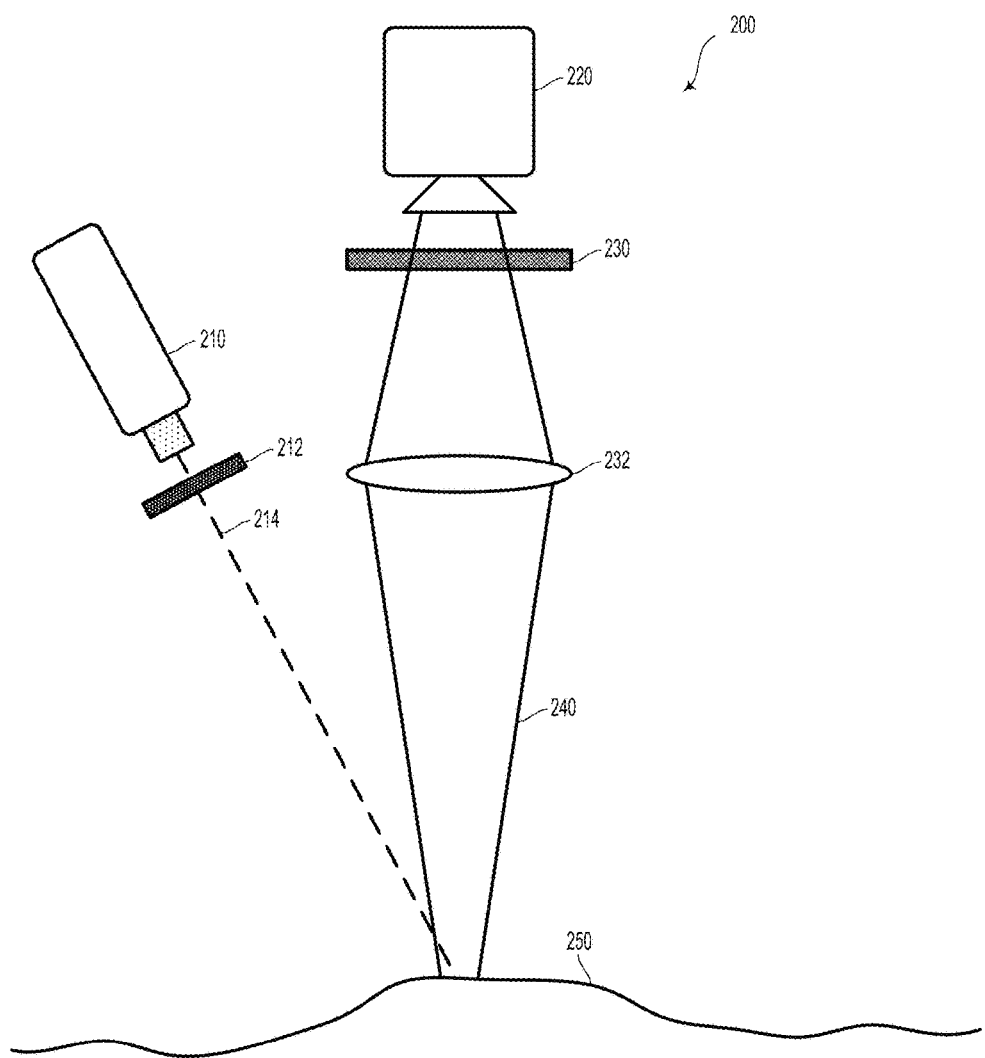
FIG. 2A illustrates a depth-mapping scenario according to an example embodiment.
Figure 2B:
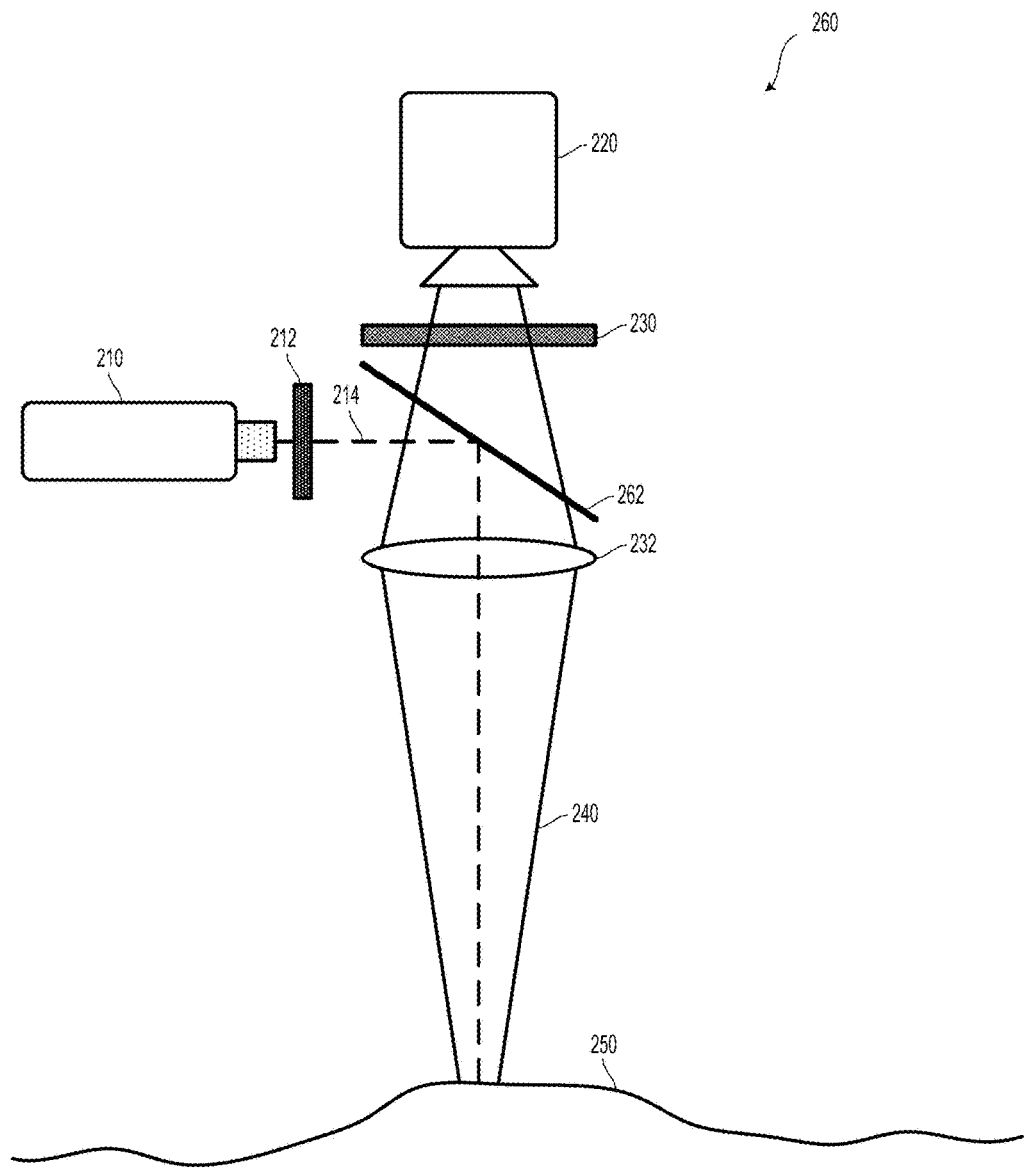
FIG. 2B illustrates a depth-mapping scenario according to an example embodiment.
Figure 2C:
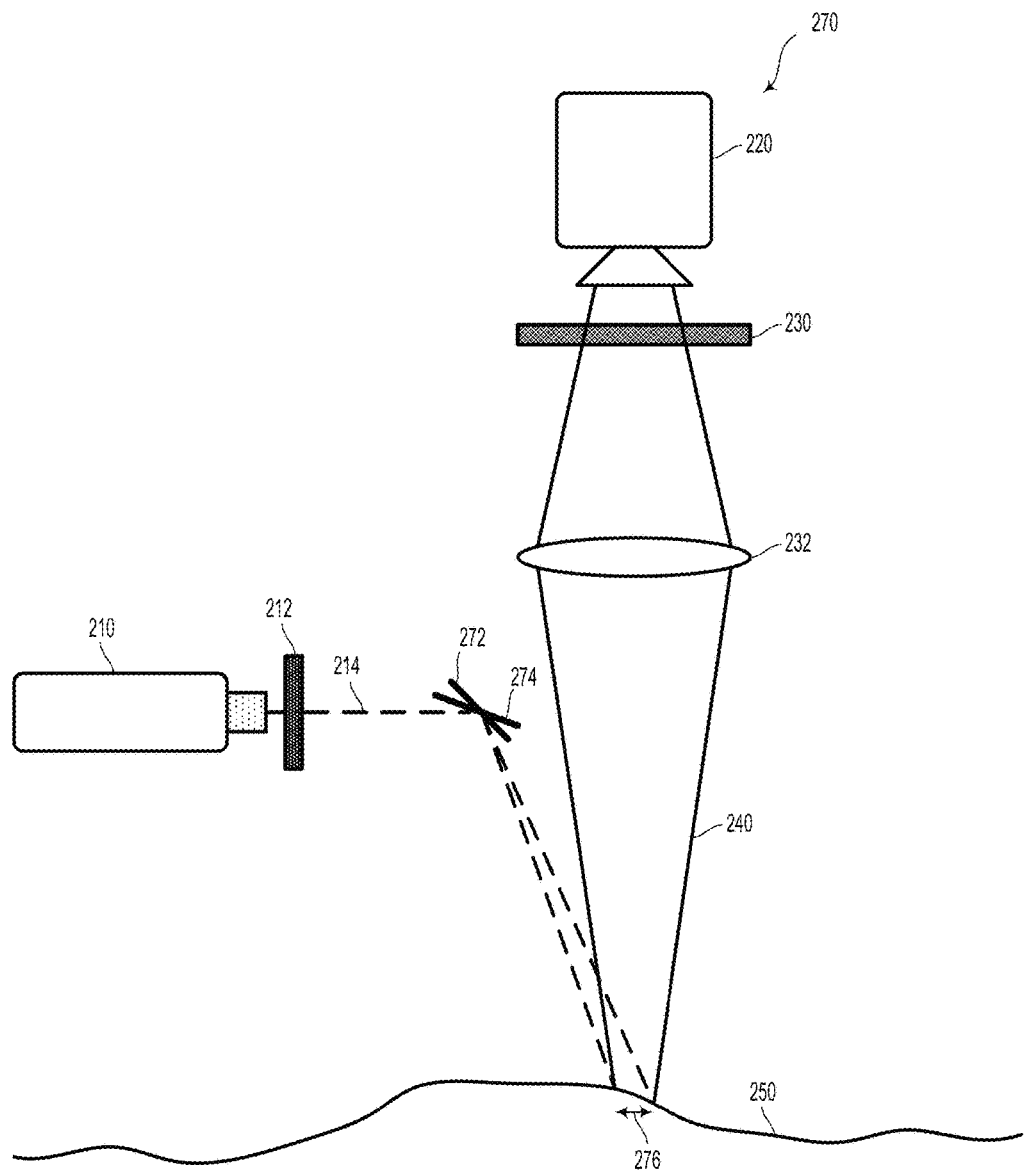
FIG. 2C illustrates a depth-mapping scenario according to an example embodiment.

FIGS. 2A, 2B, and 2C illustrate several example arrangements involving the systems and methods disclosed herein. FIG. 2A illustrates a depth-mapping scenario 200 according to an example embodiment. Depth-mapping scenario 200 includes a laser light source 210 and an image sensor 220. Laser light source 210 and image sensor 220 may be similar or identical to the corresponding elements illustrated and described with regard to FIG. 1A. Specifically, laser light source 210 may emit a laser beam 214 that impinges on a surface 250 in a field of view. The laser beam 214 may pass through a medium and/or an optical element 212. Optical element 212 may be a lens, a filter, a diffuser, an aperture or another type of optical element. The laser beam 214 may cause a characteristic speckle pattern to be observable on surface 250.

In an example embodiment, surface 250 may include tissue, such as skin tissue, or another type of surface. Image sensor 220 may include a camera configured to capture still and/or video images of surface 250. The optical path 240 for image sensor 220 may include a filter 230 and/or a lens 232.

In an example embodiment, the laser light source 210 may be configured to provide a laser beam 214 that substantially fills the field of view of image sensor 220. In such a scenario, one image may be captured by image sensor 220 to provide a depth map.

FIG. 2B illustrates a depth-mapping scenario 260 according to an example embodiment. Depth-mapping scenario may include a coaxial optical path for the laser beam 214 and imaging field of view. In such a scenario, the optical system may include a mirror 262 configured to at least partially reflect the laser beam 214 so as to direct it toward the surface 250 along substantially the same optical axis as the image sensor 220. In some embodiments, the optical path for the laser beam 214 and the image sensor 220 may be shared via one or more optical fibers, for example.

FIG. 2C illustrates a depth-mapping scenario 270 according to an example embodiment. As illustrated in depth-mapping scenario 270, the laser beam 214 may be scanned around a field of view. For example, a position of a mirror may be adjusted between a first position 272 and a second position 274 so as to direct the laser beam 214 along a sweep distance 276. In such embodiments, multiple images may need to be captured by image sensor 220 to obtain enough information to form a complete depth map of the field of view. Such image captures, and laser beam scanning, may be performed in a raster fashion. Other ways of moving the laser beam 214 and capturing characteristic speckle patterns are possible.

Figure 3:
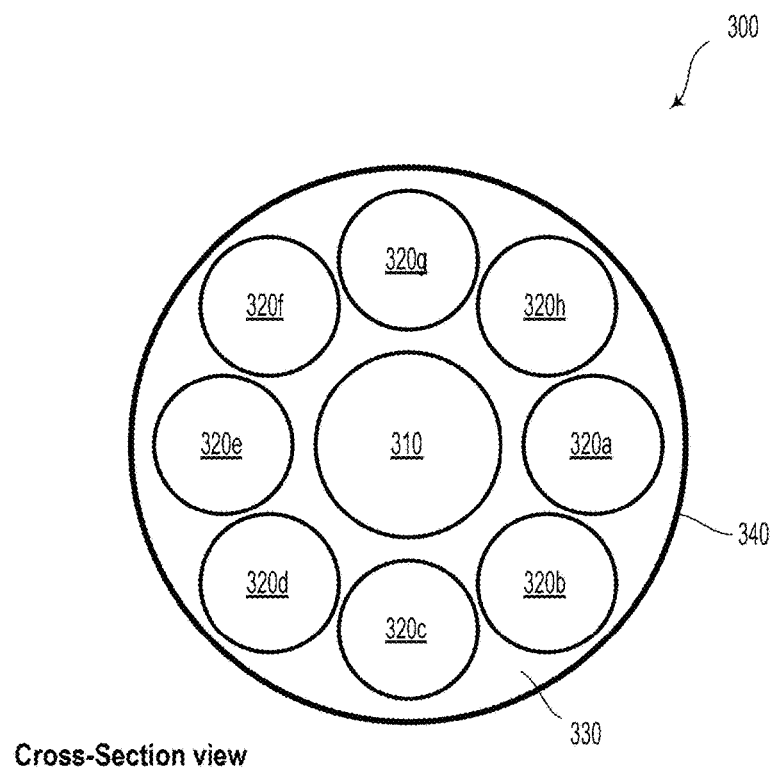
FIG. 3 illustrates several views of a portion of an endoscope according to an example embodiment.
Figure 3:
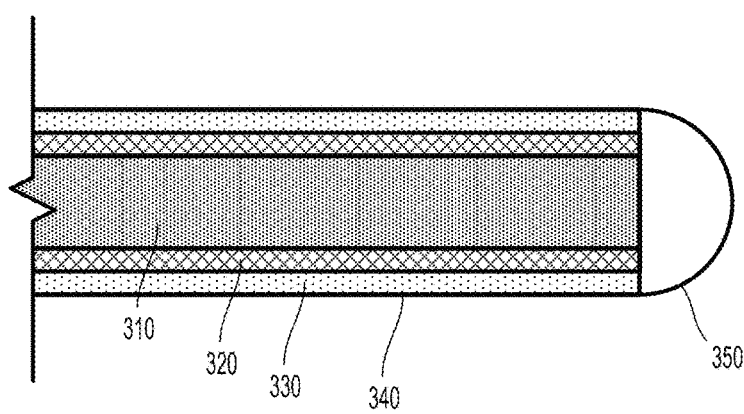

FIG. 3 illustrates several views of a portion of an endoscope 300 according to an example embodiment. For example, the endoscope 300 may include a central camera port 310 and a plurality of satellite ports 320a-h. The endoscope 300 includes an outer jacket 340 and interstitial space 330. In such a scenario, the field of view may be illuminated via the endoscope and/or the image frame may be captured via the endoscope.

The central camera port 310 may include an optical fiber for imaging a surface (e.g., tissue, a body cavity, or an organ) of a patient. Additionally or alternatively, the image sensor may be located at a distal end (e.g., end cap 350) of the endoscope 300. The satellite ports 320a-h may include one or more optical fibers for one or more laser light sources, ports for surgical tools, medical device delivery, gas or liquid delivery, suction, etc. The interstitial space 330 may include a flexible material. Endoscope 300 may include an optical lens 350 or another type of end cap.

As described elsewhere herein, at least one of the satellite ports 320a-h may include an optical fiber coupled to a high-power surgical cutting laser. In such a scenario, the surgical laser may be configured to illuminate at least a portion of the field of view based on the depth map. That is, at least one aspect of the surgical cutting laser beam may be controlled based on the depth map, such as laser beam focus, output power, wavelength, or pulse time may be controlled based on the depth map.

While FIG. 3 illustrates a certain arrangement of the central camera port 310 and satellite ports 320a-h, it is understood that other arrangements are possible within the context of endoscope ports.

Figure 4A:
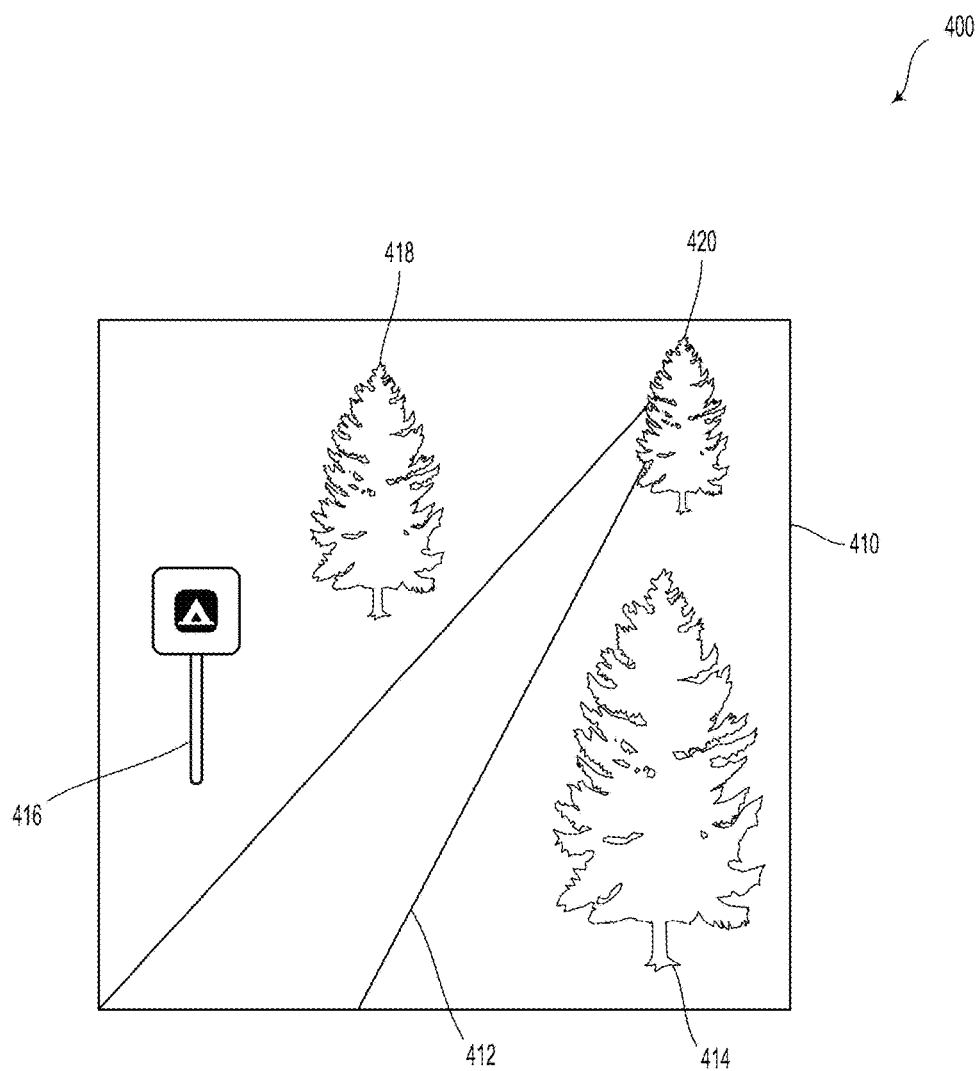
FIG. 4A illustrates a scene according to an example embodiment.

FIG. 4A illustrates a scene 400 according to an example embodiment. Scene 400 may include a field of view 410 that includes a path 412, a sign 416, and several trees 414, 418, and 420. In particular, tree 414 may represent a close object, while sign 416 and tree 418 may represent middle depth objects. Furthermore, tree 420 may represent a distant object and path 412 may exist in the foreground as well as stretch into the distance.

Figure 4B:
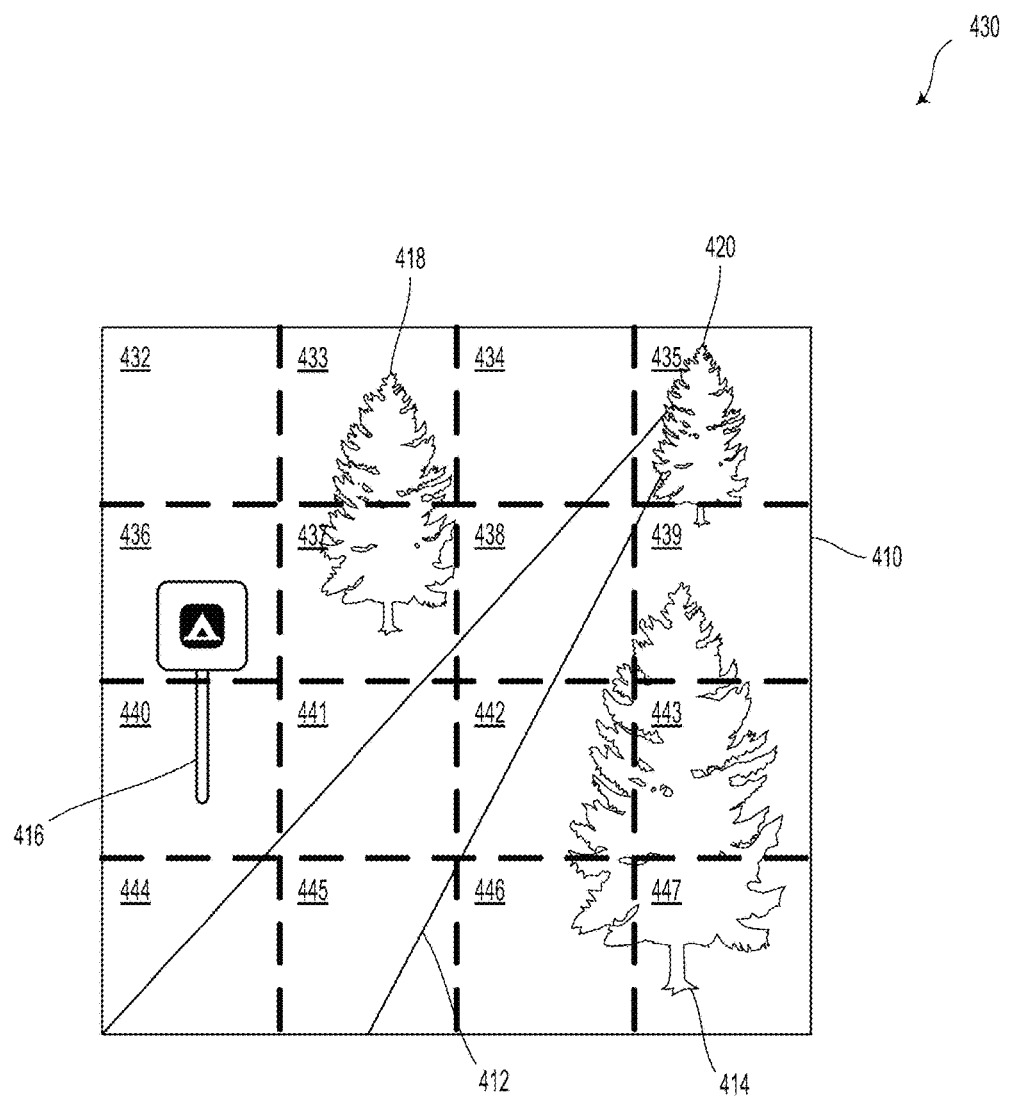
FIG. 4B illustrates a depth-mapping scenario according to an example embodiment.

FIG. 4B illustrates a depth-mapping scenario 430 according to an example embodiment. Depth-mapping scenario 430 includes partitioning the scene 400 into a plurality of image segments 432-447. In this case, the scene 400 may be divided into sixteen equal segments. In other embodiments, different numbers of image segments are possible. For example, a square image frame may be divided up into a 64×64 array.

Additionally or alternatively, the partitioning may be performed in more than one step. For example, an initial "rough" partitioning may be performed, followed by increasingly "fine" partitioning steps. The fine partitioning may be performed based on an estimated distance relating to the image segment. Furthermore, the partitioning steps need not be static, but may occur dynamically based on, for example, image recognition algorithms applied to the captured image frame. That is, image partitioning may be initially based on pixels having similar color, intensity, shape, etc. In such a scenario, trees 414, 418, and 420 may each make up an image segment.

In an example embodiment, multiple partition steps and autocorrelation steps may be performed on the same image frame. For example, a first depth map may be found based on a first partition arrangement. In such a scenario, a second partition of the same image frame could be performed. The second partition arrangement may include a shifted set of image segments (e.g., in x and/or y) and/or may include a different number of image segments (e.g., by making the image segments smaller or larger). A second set of autocorrelations may be obtained based on the second arrangement of image segments. Such a multi-partition/autocorrelation method may provide better identification of depth/distance changes within the field of view.

In some cases, the size and/or number of image segments may be determined based on a noise level of the image frame. That is, if the image frame is noisy, the partitioning step may result in larger image segments compared to if the noise level of the image frame is low. As such, image frames offering lower levels of noise may able to provide more reliable autocorrelation data. Therefore, if an image frame has relatively less noise, a higher resolution depth map may be possible, all other variables being equal.

Figure 4C:
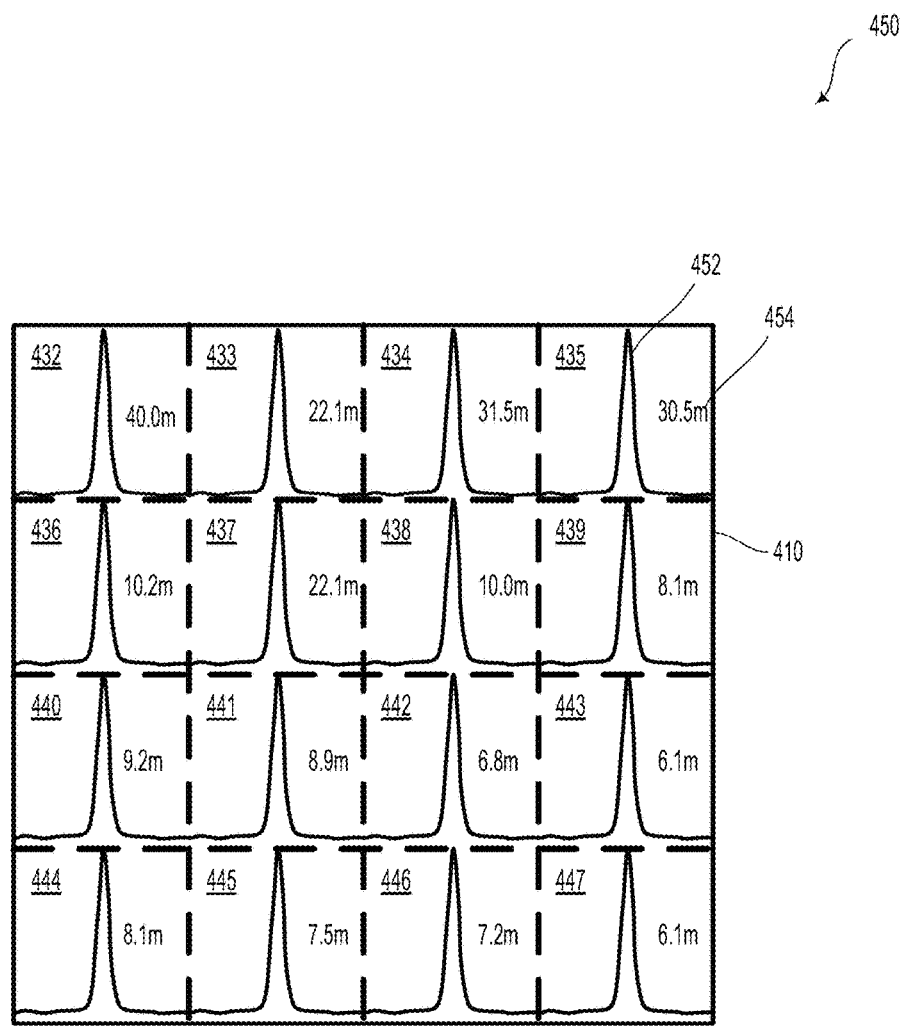
FIG. 4C illustrates a depth map according to an example embodiment.

FIG. 4C illustrates a depth map 450 according to an example embodiment. The depth map 450 includes a graphical representation of the autocorrelation result for each image segment 432-447 and an estimated local distance to the object or objects within the respective image segments. For example, for image segment 435, a graphical representation 452 of the autocorrelation may be included. The graphical representation 452 may be similar or identical in kind to autocorrelation data 192 as illustrated and described in reference to FIG. 1C. However, other types of graphical representations, such as the two-dimensional graphical representation of autocorrelation result 180 as illustrated and described in reference to FIG. 1B, are also possible.

The depth map 450 may additionally or alternatively display an estimated distance value 454. The estimated distance value 454 may represent the distance calculated based on the autocorrelation of the respective image segment. For example, in image segment 435, the estimated distance value 454 may be 30.5 meters, which may correspond with the distance to tree 420.

While FIG. 4C illustrates the depth map 450 as including numerical values for the estimated distance value 454, it is understood that such information may be displayed or conveyed in a variety of different ways. For example, each image segment may be assigned a color from a color map based on the respective estimated distance value. Additionally or alternatively, each image segment of depth map 450 may be assigned a grayscale value based on the relative estimated distance value. Other types of representations are possible.

Systems disclosed herein may provide live depth maps during a surgical procedure. For example, the systems described here may provide a real-time analysis of tumor or other tissue removal using a surgical cutting laser. Other surgical, and non-surgical, applications involving distance/depth mapping are contemplated herein.

Method Examples

Figure 5:
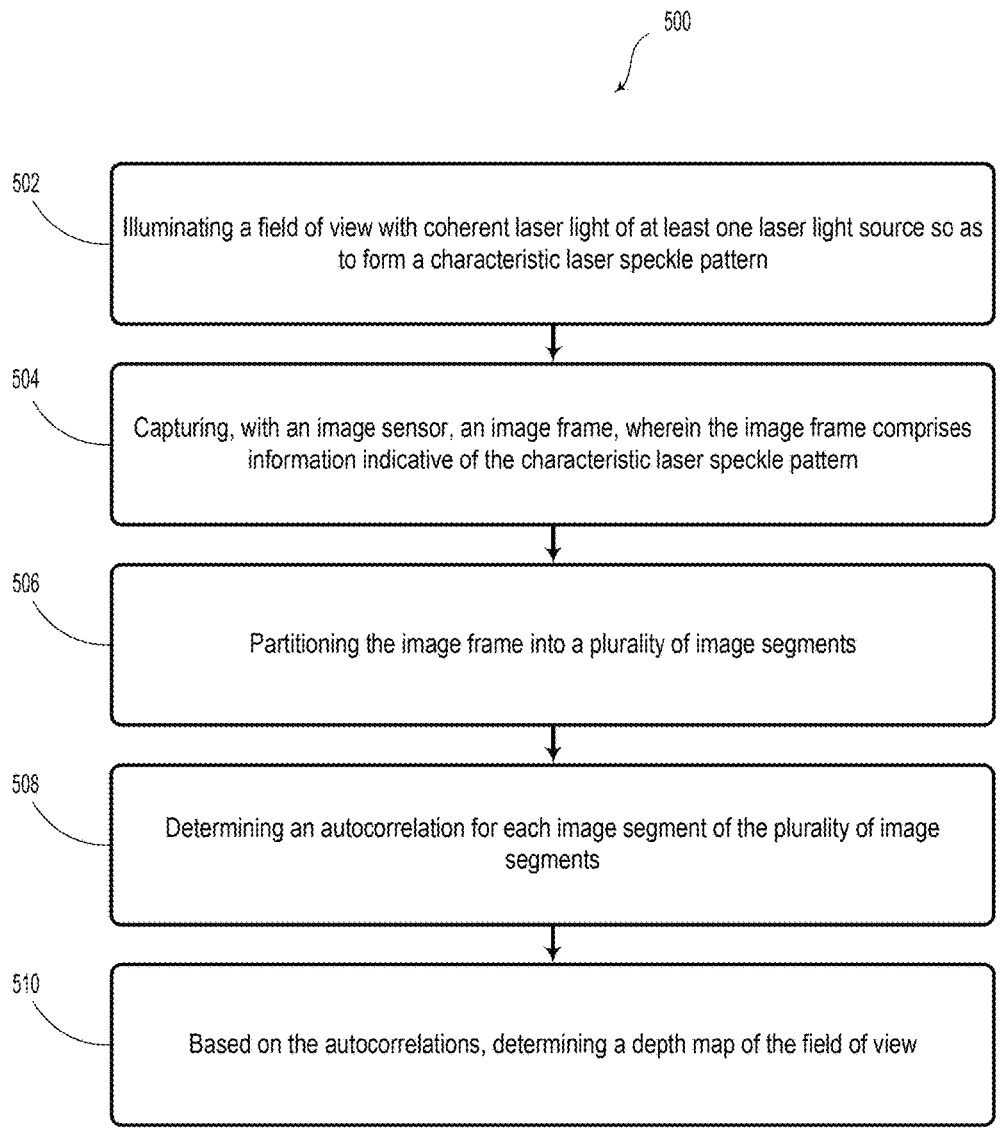
FIG. 5 is a flowchart illustrating a method according to an example embodiment.

FIG. 5 is a flowchart illustrating a method according to an example embodiment. The method 500 includes blocks that may be carried out in any order. Furthermore, various blocks may be added to or subtracted from method 500 within the intended scope of this disclosure. The method 500 may correspond to blocks that may be carried out using any or all of the devices and/or systems illustrated and described in reference to FIG. 1A, 2A, 2B, 2C, or 3. In some embodiments, controller 140 may be configured to carry out at least some of the blocks disclosed herein.

Block 502 includes illuminating a field of view with coherent laser light of at least one laser light source so as to form a characteristic laser speckle pattern. In an example embodiment, the laser light source, which may be similar or identical to laser light source 110 as described in relation to FIG. 1A, may illuminate an entire field of view with coherent laser light so as to form the characteristic speckle pattern.

In some embodiments, the laser light source may emit a plurality of laser wavelengths. In such a scenario, the characteristic laser speckle pattern may include at least two laser wavelengths from the plurality of laser wavelengths.

Furthermore, the laser light source may be configured to illuminate the field of view by a scanning technique. For example, a movable mirror may be controlled so as to cause the laser beam to impinge on a desired portion of the field of view.

Block 504 includes capturing, with an image sensor, an image frame. The image sensor may be similar or identical to image sensor 120 as illustrated and described with regard to FIG. 1A. Specifically, the image frame may include information indicative of the characteristic laser speckle pattern.

Block 506 includes partitioning the image frame into a plurality of image segments.

Block 508 includes determining an autocorrelation for each image segment of the plurality of image segments. In an example embodiment, determining the autocorrelation for each image segment may include determining a power spectrum of the respective image segment. That is, the power spectrum of the respective image segment may be found based on solving for a square of a Fourier transform of an image intensity of the respective image segment.

In an example embodiment, the autocorrelation information may be averaged over at least two corresponding image segments (e.g., from successive image frames) so as to provide a more robust and reliable distance estimate.

Block 510 includes, based on the autocorrelations, determining a depth map of the field of view. The depth map may be similar or identical to that illustrated and described with regard to FIG. 4C, however other types of depth maps are possible.

In an example embodiment, the methods described herein may be applied to procedures involving an endoscope. For example, a surgical field of view (e.g., in a lumen, in a body cavity) may be illuminated via an endoscope. Correspondingly, image frames may be captured via the endoscope.

As described elsewhere herein, the depth mapping functions may be used to control or otherwise adjust other surgical procedures or devices. For example, a surgical laser may illuminate (e.g., ablate tissue) at least a portion of the field of view based on the depth map. For instance, the surgical laser may be focused or steered based on information in the depth map.

The systems and methods described herein may include obtaining depth map information under varying optical conditions. That is, a first depth map may be computed under a first set of conditions and a second depth map may be computed under a second set of conditions. By computing multiple depth maps under slightly different conditions, the distance estimates from the depth maps may be averaged and may represent more robust and/or reliable distance information.

By way of example, a first image frame may be captured with the at least one laser light source at a first position. Thereafter, the position of the laser light source may be adjusted and a second image frame may be captured.

Additionally or alternatively, a first image frame may be captured without a diffuser in the optical path between the laser light source and the field of view. A subsequent second image frame may be captured after interposing such a diffuser in the optical path.

In another embodiment, a first image frame may be captured under a first operating condition of the laser light source. Subsequently, the operating condition of the laser light source may be adjusted and a second image frame may be captured.

It is understood that a variety of other elements may be adjusted so as to provide a slightly different characteristic speckle pattern. Each different speckle pattern may have a unique set of attributes, which should still result in a materially similar depth map (assuming basic optical geometries have stayed the same or that such movements have been accounted for).

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

While various examples and embodiments have been disclosed, other examples and embodiments will be apparent to those skilled in the art. The various disclosed examples and embodiments are for purposes of illustration and are not intended to be limiting, with the true scope being indicated by the following claims.

What is claimed is:

1. A system, comprising:
   at least one laser light source;
   an image sensor; and
   a controller comprising a memory and at least one processor, wherein the at least one processor executes instructions stored in the memory to carry out operations, wherein the operations comprise:

causing the at least one laser light source to illuminate a field of view with coherent laser light so as to form a characteristic laser speckle pattern;

causing the image sensor to capture an image frame, wherein the image frame comprises information indicative of the characteristic laser speckle pattern;

partitioning the image frame into a plurality of image segments;

determining an autocorrelation for each image segment of the plurality of image segments; and based on the autocorrelations, determining a depth map of the field of view.

2. The system of claim 1, wherein determining the autocorrelation for each image segment comprises determining a power spectrum of the respective image segment, wherein the power spectrum of the respective image segment comprises a square of a Fourier transform of an image intensity of the respective image segment.

3. The system of claim 1, wherein the image frame is one image frame from a plurality of image frames of the field of view, wherein determining the depth map of the field of view comprises averaging the autocorrelations of corresponding image segments of the plurality of image frames.

4. The system of claim 1, wherein the at least one laser light source emits a plurality of laser wavelengths, wherein the characteristic laser speckle pattern comprises at least two laser wavelengths from the plurality of laser wavelengths.

5. The system of claim 1, further comprising an endoscope, wherein the field of view is illuminated via the endoscope or the image frame is captured via the endoscope.

6. The system of claim 1, further comprising a surgical laser, wherein the operations further comprise causing the surgical laser to illuminate at least a portion of the field of view based on the depth map.

7. The system of claim 1, wherein causing the at least one laser light source to illuminate the field of view comprises scanning the at least one laser light source over the field of view.

8. The system of claim 1, wherein the operations further comprise at least one of: moving a position of the at least one laser light source, interposing a moving diffuser between the at least one laser light source and the field of view, adjusting an optical path of light emitted by the at least one light source to illuminate the field of view, or adjusting an operating condition of the at least one laser light source.

9. A method utilizing the system of claim 1, wherein the method comprises determining a depth map of a portion of a patient during a surgical procedure.

10. A method, comprising:

illuminating a field of view with coherent laser light of at least one laser light source so as to form a characteristic laser speckle pattern;

capturing, with an image sensor, an image frame, wherein the image frame comprises information indicative of the characteristic laser speckle pattern;

partitioning the image frame into a plurality of image segments;

determining an autocorrelation for each image segment of the plurality of image segments; and based on the autocorrelations, determining a depth map of the field of view.

11. The method of claim 10, wherein determining the autocorrelation for each image segment comprises determining a power spectrum of the respective image segment, wherein the power spectrum of the respective image segment comprises a square of a Fourier transform of an image intensity of the respective image segment.

12. The method of claim 10, wherein the image frame is one image frame from a plurality of image frames of the field of view, wherein determining the depth map of the field of view comprises averaging the autocorrelations of corresponding image segments of the plurality of image frames.

13. The method of claim 10, wherein the at least one laser light source emits a plurality of laser wavelengths, wherein the characteristic laser speckle pattern comprises at least two laser wavelengths from the plurality of laser wavelengths.

14. The method of claim 10, wherein the field of view is illuminated via an endoscope.

15. The method of claim 10, wherein the image frame is captured via an endoscope.

16. The method of claim 10, further comprising illuminating, with a surgical laser, at least a portion of the field of view based on the depth map.

17. The method of claim 10, wherein illuminating the field of view with coherent laser light comprises scanning the at least one laser light source over the field of view.

18. The method of claim 10, further comprising, capturing a second image frame after moving a position of the at least one laser light source.

19. The method of claim 10, further comprising, capturing a second image frame after interposing a diffuser between the at least one laser light source and the field of view.

20. The method of claim 10, further comprising, capturing a second image frame after adjusting an operating condition of the at least one laser light source.

* * * * *